US008088756B2

(12) United States Patent
Bauer

(10) Patent No.: US 8,088,756 B2
(45) Date of Patent: Jan. 3, 2012

(54) METHODS AND COMPOSITIONS FOR ORAL DELIVERY OF FTS

(75) Inventor: Victor J. Bauer, Bridgewater, NJ (US)

(73) Assignee: Concordia Pharmaceuticals, Inc., Fort Lauderdale, FL (US)

( * ) Notice: Subject to any disclaimer, the term of this patent is extended or adjusted under 35 U.S.C. 154(b) by 1223 days.

(21) Appl. No.: 11/659,582

(22) PCT Filed: Aug. 18, 2005

(86) PCT No.: PCT/US2005/029389
§ 371 (c)(1),
(2), (4) Date: Feb. 7, 2007

(87) PCT Pub. No.: WO2006/023639
PCT Pub. Date: Mar. 2, 2006

(65) Prior Publication Data
US 2009/0226512 A1    Sep. 10, 2009

Related U.S. Application Data

(60) Provisional application No. 60/602,361, filed on Aug. 18, 2004.

(51) Int. Cl.
*A01N 37/36* (2006.01)
*A01N 31/00* (2006.01)
(52) U.S. Cl. ........................... 514/159; 514/713
(58) Field of Classification Search ................ 514/159, 514/713
See application file for complete search history.

(56) References Cited

U.S. PATENT DOCUMENTS

| 5,145,684 | A | * | 9/1992 | Liversidge et al. ........... 424/489 |
| 5,705,528 | A | | 1/1998 | Kloog |
| RE39,682 | E | | 1/2001 | Kloog |
| 6,462,086 | B1 | | 10/2002 | Kloog et al. |
| 2003/0153521 | A1 | * | 8/2003 | McSwiggen .................... 514/44 |
| 2003/0203942 | A1 | * | 10/2003 | Kloog et al. .................. 514/350 |
| 2004/0072258 | A1 | | 4/2004 | Kloog et al. |

FOREIGN PATENT DOCUMENTS

| EP | 2218451 A1 | 8/2010 |
| EP | 2301528 A1 | 3/2011 |
| WO | 95/13059 A1 | 5/1995 |
| WO | 00/78303 A1 | 12/2000 |
| WO | WO-2004/083458 A | 9/2004 |
| WO | WO-2004/103352 A | 12/2004 |
| WO | 2005/018562 A2 | 3/2005 |
| WO | 2006/023639 A1 | 3/2006 |
| WO | 2007/064448 | 6/2007 |

OTHER PUBLICATIONS

Christoph Schmidt & Roland Bodmeier, Incorporation of Polymeric Nanoparticles into Solid Dosage Forms, 57 J Control. Rel. 115 (1999).*
Marom M et al: Journal of Biological Chemistry, American Society for Biochemistry and Molecular Biology, Inc, 270(38); 22263-22270 (1995), XP002911 074.
Smalley Keiran S M et al: International Journal of Cancer, 98(4); 514-522 (2002), XP002511701.
McPherson R A et al: Prostate, 58(4); 325-334 (2004), XP009084055.
Jansen B et al: Proceedings of the National Academy of Sciences of the United States of America, 96(24); 14019-14024 (1999).
Aharonson Z et al: Biochimica et Biophysica Acta Molecular Basis of Disease, Amsterdam, NL LNKD-DOI, 1406(1); 40-50 (1998), XP004276706.
European Search Report, EP 10004111, dated Jun. 6, 2010.
Weisz B, Giehl K & Gana-Weisz M et al:Oncogene, 18: 2579-2588 (1999).
Blum et al.: Cancer Res., 65(3): 999-1006 (2005).
Beiner M E et al: "Ras Antagonist Inhibits Growth and Chemosensiuzes Human Epitheliaf Ovarian Cancer Cells" International Journal of Gynecological Cancer, Blackwell Scientific Publicattons, Cambridge, MA, US, vol. 16, No. suppl 1, Jan. 2006, pp. 200-206.
International Search Report, PCT/IL2007/001556, dated May 2, 2008.
Zundelevich, Adi et al, "Suppression of lung cancer tumor growth in a nude mouse model by the Ras inhibitor salirasib (farnesylhiosalicylic acid)." Molecular Cancer Therapeutics' Jun. 2007, vol. 6, No. 6, pp. 1765-1773.
Dorwald (Side Reactions in Organci Synthesis: A guide to successful synthesis design, Weinheim: Wiley-VCH, Verlag Gmbh & co. KGaA, 2005, Preface.
Hirose et al. Phase I study of the combination of gemcitabine and nedaplatin for treatment of previously untreated advanced non-small cell lung cancer. Lung Cancer, 39, 2003, 91-97.
Sandler et al. Phase III trail of gemcitabine plus cisplatin verus cisplatin alone in patients with locally advanced or metastatic non-small cell lung cancer. Journal of Clinical Oncology, vol. 18, No. 1, Jan. 2000, pp. 122-130.
European Search Report, EP 10183723, dated Jan. 27, 2011.
Lachman et al., The Theory and Practice of Industrial Pharmacy: Second Edition, p. 342 (1976).
Rudnic et al, Remington: The Science and Practice of Pharmacy: 20th Edition, pp. 858-863 (2000).
Halaschek-Wiener et al., "Franesyl Thiosaliciylic Acid Chemosensitiezes Human Melanoma In Vivo", The Journal of Investigative Dermatology, pp. 1-7 (2003).
Gana-Weisz et al., Clinical Cancer Research; 8; 555-565 (2002).
International Search Report, PCT/US05/29389, dated Jan. 17, 2006.

\* cited by examiner

*Primary Examiner* — Karlheinz R Skowronek
*Assistant Examiner* — Sean Basquill
(74) *Attorney, Agent, or Firm* — Lerner, David, Littenberg, Krumholz & Mentlik, LLP

(57) ABSTRACT

Disclosed are oral dosage forms containing a Ras antagonist including FTS and structural analogs thereof, and at least one pharmaceutically acceptable excipient other than a cyclodextrin, and methods of orally administering same to treat diseases and disorders responsive to the Ras antagonists.

10 Claims, 4 Drawing Sheets

Plasma Concentration for FTS in Corn Oil

Plasma Concentration (ng./ml.) for FTS in 0.5% CMC

METHODS AND COMPOSITIONS FOR ORAL DELIVERY OF FTS

CROSS REFERENCE TO RELATED APPLICATIONS

The present application is a national phase entry under 35 U.S.C. §371 of International Application No. PCT/US2005/029389, filed Aug. 18, 2005, published in English, which claims benefit of U.S. Provisional Patent Application No. 60/602,361, filed Aug. 18, 2004. The disclosures of all of said applications are incorporated by reference herein.

BACKGROUND OF THE INVENTION

U.S. Pat. No. 5,705,528 teaches farnesylthiosalicyclic acid (FTS) and analogs thereof and their utility as anti-cancer agents. U.S. Pat. No. 6,462,086 teaches additional therapeutic utilities of these compounds, namely in connection with treatment of non-malignant diseases, pathological states or other disorders that feature or otherwise include Ras-induced proliferation of cells. The patent also teaches that these compounds are inactive when administered orally, but that this shortcoming can be overcome by making a salt of the compound (i.e., salification), formulating the salt in cyclodextrin, and then preparing a buccal tablet (which will dissolve in the mouth when held against the mucous membrane).

SUMMARY OF THE INVENTION

Applicants have discovered that FTS and its analogs do not require salification or formulation in cyclodextrin to be active upon oral administration.

A first aspect of the present invention is directed to an oral dosage form comprising an amount of a Ras antagonist effective to treat a responsive disease or disorder involving abnormal cell proliferation, and a pharmaceutically acceptable carrier other than a cyclodextrin, wherein said Ras antagonist is represented by the formula (I)

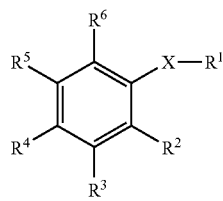

wherein:
$R^1$ represents farnesyl, geranyl or geranyl-geranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy, or alkylmercapto; and
X represents S. The oral dosage forms are tablets or capsules. In preferred embodiments, the Ras antagonist is not in the form of a salt.

A second aspect of the invention is directed to method of treating a treating a disease or disorder involving abnormal cell proliferation, comprising administering to a human subject in need thereof an oral dosage form comprising an amount of a Ras antagonist effective to treat the disease or disorder, and a pharmaceutically acceptable carrier other than a cyclodextrin, wherein said Ras antagonist is represented by the formula

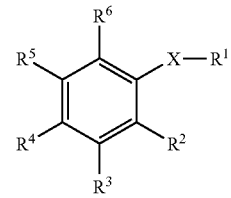

wherein:
$R^1$ represents farnesyl, geranyl or geranyl-geranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy, or alkylmercapto; and
X represents S.

DETAILED DESCRIPTION

Figure 1:
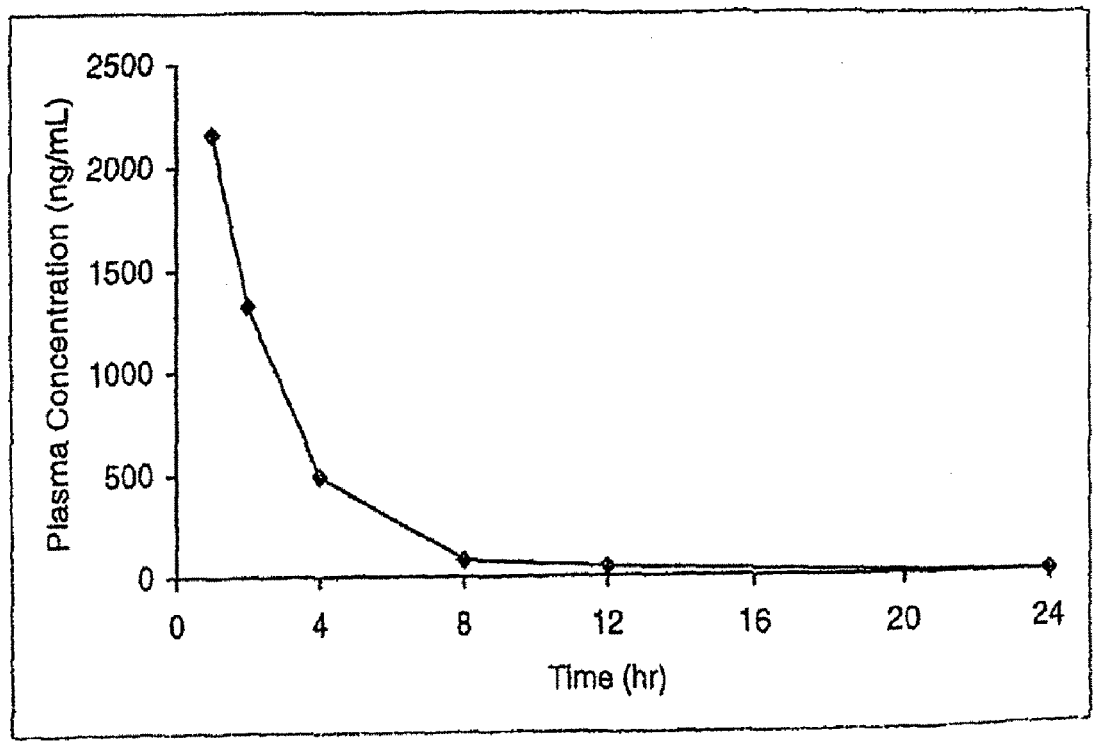
FIG. 1 is a graph showing concentrations (ng/mL) of FTS in plasma of mice over time following oral (e.g., gavage) administration of FTS in a corn oil carrier.

Ras antagonists useful in the present invention are represented by formula I:

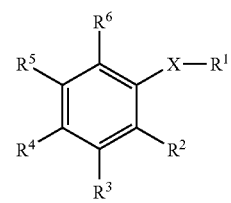

wherein
$R^1$ represents farnesyl, geranyl or geranyl-geranyl;
$R^2$ is $COOR^7$, or $CONR^7R^8$, wherein $R^7$ and $R^8$ are each independently hydrogen, alkyl or alkenyl;
$R^3$, $R^4$, $R^5$ and $R^6$ are each independently hydrogen, alkyl, alkenyl, alkoxy, halo, trifluoromethyl, trifluoromethoxy, or alkylmercapto; and
X represents S.

These compounds represent farnesyl-thiosalicylic acid (FTS) (i.e., S-trans, trans-FTS) and its analogs. The structure of FTS is as follows:

FTS:

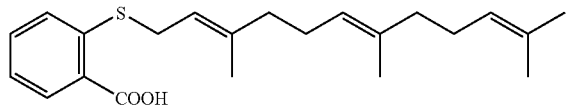

FTS analogs embraced by formula I include 5-fluoro-FTS, 5-chloro-FTS, 4-chloro-FTS and S-farnesyl-thiosalicylic acid methyl ester (FTSME). Structures of these compounds are set forth below.

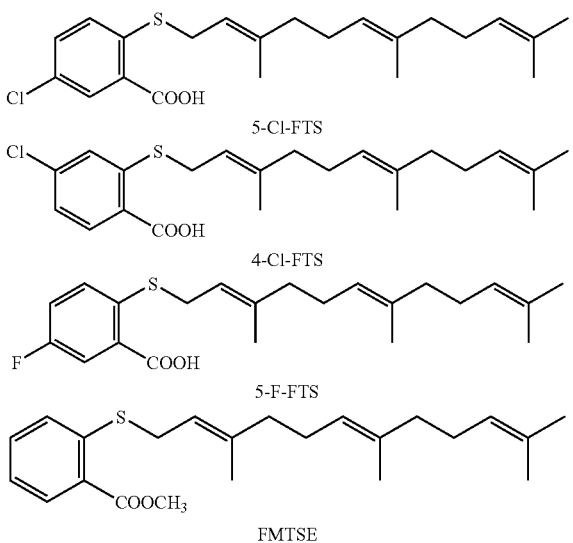

5-Cl-FTS

4-Cl-FTS

5-F-FTS

FMTSE

Pharmaceutically acceptable salts of the Ras antagonists of formula I may be useful. In preferred embodiments, however, the Ras antagonist is not in the form of a salt (i.e., non-salified).

Methods of preparing the compounds of formula I are disclosed in U.S. Pat. Nos. 5,705,528 and 6,462,086. Those disclosures (e.g., Example 7 in the '086 patent) are incorporated herein by reference.

Oral dosage forms useful in the present invention include tablets (e.g., including film-coated, sugar-coated, controlled or sustained release), and capsules, e.g., hard gelatin capsules (including controlled or sustained release), and soft gelatin capsules.

Oral dosage forms may be prepared by mixing the active pharmaceutical ingredient, which in this case are the Ras antagonists of formula I, with one or more appropriate carriers (excipients), and then formulating the composition into the desired dosage form e.g., compressing the composition into a tablet or filling into a capsule. The proviso is that the oral dosage forms do not contain a cyclodextrin. Typical excipients useful as bulking agents or diluents, binders, buffers or pH adjusting agents, disintegrants (including crosslinked and super disintegrants such as croscarmellose), glidants, and/or lubricants include lactose, starch, mannitol, microcrystalline cellulose, ethyl cellulose, sodium carboxymethyl cellulose, hydroxypropylmethyl cellulose, dibasic calcium phosphate, acacia, gelatin, stearic acid, magnesium stearate, corn oil, vegetable oils, and polyethylene glycols, and others known to the pharmaceutical practitioner. Coating agents such as sugar, shellac, and synthetic polymers may be employed. Dyes and other colorants may be added as well. See, *Remington's Pharmaceutical Sciences*, The Science and Practice of Pharmacy, 20th Edition, (2000).

The oral dosage forms of the present invention are useful in treating diseases and disorders responsive to the Ras antagonists of formula I, e.g., diseases and disorders characterized or mediated, at least in part, by abnormal (e.g., uncontrolled) cell proliferation, such as Ras-induced cell proliferation. The proliferating cells may be malignant or non-malignant in nature. Of course, the term "responsive" does not require that a therapeutic response would be achieved in each and every patient, but rather what a skilled practitioner would reasonably expect based on existing data from patient populations. These diseases and disorders include cancers including breast cancer, colon cancer, glioblastoma, lung cancer (small cell and non-small cell lung cancer), melanoma, Merkel cell carcinoma, neuroblastoma, neurofibromatosis, ovarian cancer, pancreatic cancer and prostate cancer.

Examples of non-malignant diseases and disorders characterized by or involving abnormal (e.g., uncontrolled) cell proliferation include liver cirrhosis, restenosis after angioplasty (post-angioplasty restenosis), atherosclerosis, and graft rejection (e.g., graft-versus-host disease (GVHD)). Other examples include autoimmune diseases such as type-1 diabetes mellitus, systemic lupus erythematosis, rheumatoid arthritis, psoriasis, multiple sclerosis, Guillain-Barre syndrome and primary antiphospholipid syndrome.

As used herein, the term "effective amount" refers to a dosage of the Ras antagonist that inhibits disease onset or progression or ameliorates symptom(s) of the disease. The typical daily dose is 5 mg to 1000 mg, e.g., 100 mg to 1,000 mg per day, which may be administered once daily or as divided doses two or three times daily. Thus, the oral dosage forms of the present invention e.g., tablet, hard gelatin capsule, or soft gelatin capsule, typically contains from 5 mg to 500 mg of the Ras antagonist. In preferred embodiments, the oral dosage forms contain from 10 mg to 250 mg of active pharmaceutical ingredient. The oral dosage forms are typically administered to an individual diagnosed with the disease or disorder, although prophylactic administration may be useful to inhibit onset of a disease or disorder e.g., administration prior to an angioplasty procedure to inhibit onset of restenosis.

The oral dosage forms may be suitably packaged for distribution and sale, including printed instructions for administering them as described herein.

The present invention will now be described by way of the following non-limiting examples. They are presented solely for purposes of illustration, and are not intended to limit the invention in any way.

EXAMPLE 1

Bioavailability of Orally Administered FTS a. FTS Formulated in Corn Oil.

FTS (40 mg) was dispersed in corn oil (10 ml). Aliquots of the resulting suspension were administered by gavage to CD-1 mice (eighteen) at a dose of 40 mg/ml (at a volume of 10 ml/kg of FTS suspension calculated for actual animal weight). Blood samples were collected in lithium heparin tubes via the retro-orbital plexus while under $CO_2/O_2$ anesthesia at 1, 2, 4, 8, 12 and 24 hours (3 animals at each time point) after dosing. Aliquots (100 μL) of plasma were mixed with water, pH 11 buffer solution and acetonitrile. After centrifugation, the supernatant was evaporated to dryness. The residue was resuspended in water/acetonitrile and centrifuged, and the supernatant was transferred to auto-sampler vials for FTS determination by liquid chromatography/mass spectrometry (LC/MS).

As shown in FIG. 1, mean plasma FTS concentrations were 2159 ng/ml at 1 hour and 1326 ng/ml after 2 hours. There was a rapid decrease to less than 3 ng/ml after 24 hours. These values indicated 55% oral bioavailability compared to intraperitoneal injection of FTS in a control group of animals.

b. FTS Formulated in 0.5% Aqueous Carboxymethylcellulose.

FTS (40 Mg) was dispersed in 0.5% aqueous carboxymethylcellulose (10 ml). Aliquots of the resulting suspension were administered by gavage to CD-1 mice (eighteen) at a dose of 40 mg/ml (at a volume of 10 ml/kg of FTS suspension calculated for actual animal weight). Blood samples were collected in lithium heparin tubes via the retro-orbital plexus while under $CO_2/O_2$ anesthesia at 1, 2, 4, 8, 12, and 24 hours (3 animals at each time point) after dosing. Aliquots (100 µL) of plasma were mixed with water, pH 11 buffer solution, and acetonitrile. After centrifugation, the supernatant was evaporated to dryness. The residue was re-suspended in water/acetonitrile and centrifuged, and the supernatant was transferred to auto-sampler vials for FTS determination by LC/MS.

Figure 2:
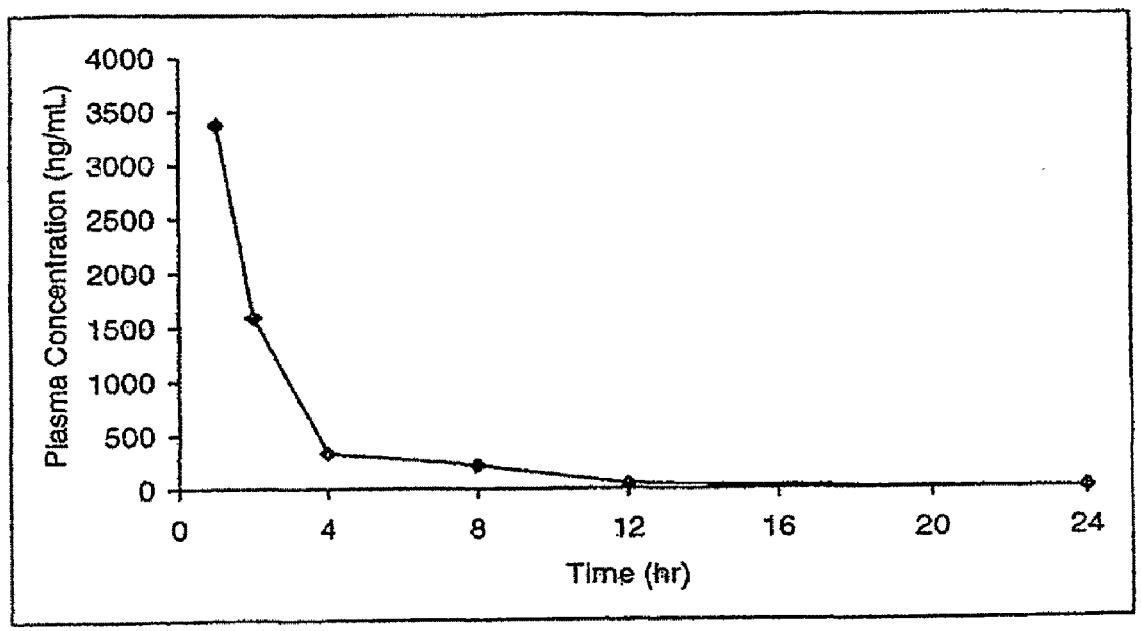
FIG. 2 is a graph showing concentrations (ng/mL) of FTS in plasma of mice over time following oral (gavage) administration of FTS in aqueous carboxymethylcellulose (CMC) carrier.

As shown in FIG. 2, mean plasma FTS concentrations were 3381 ng/ml at 1 hour, 1593 ng/ml after 2 hours, and decreased rapidly to less than 3 ng/ml after 24 hours. These values indicated 69% oral bioavailability compared to intra-peritoneal injection of FTS in a control group of animals.

These results, as illustrated in FIGS. 1 and 2, were unexpected, and in addition, show that therapeutic levels may be readily obtained upon oral administration.

EXAMPLE 2

Inhibition of Pancreatic Tumor Growth with Orally Administered FTS

Nude $CD_1$-Nu Mice were implanted subcutaneously with $5.0 \times 10^6$ Panc-1 cells in 0.2 ml of PBS just above the right femoral joint. Eleven days after implantation, palpable tumors were observed.

FTS was dispersed in 0.5% aqueous carboxymethylcellulose at a concentration of 5 mg/ml. On the eleventh day after implantation, mice were segregated into three groups and were given vehicle or FTS suspension by gavage.

Group 1 (Controls, 6 mice) received 0.2 ml vehicle daily.
Group 2 (20 mg/kg FTS, 7 mice) received 0.1 ml FTS suspension daily.
Group 3 (40 mg/kg FTS, 6 mice) received 0.2 ml FTS suspension daily.

Mice were treated for ten days, and were sacrificed. Tumors were excised and weighed.

Figure 3:
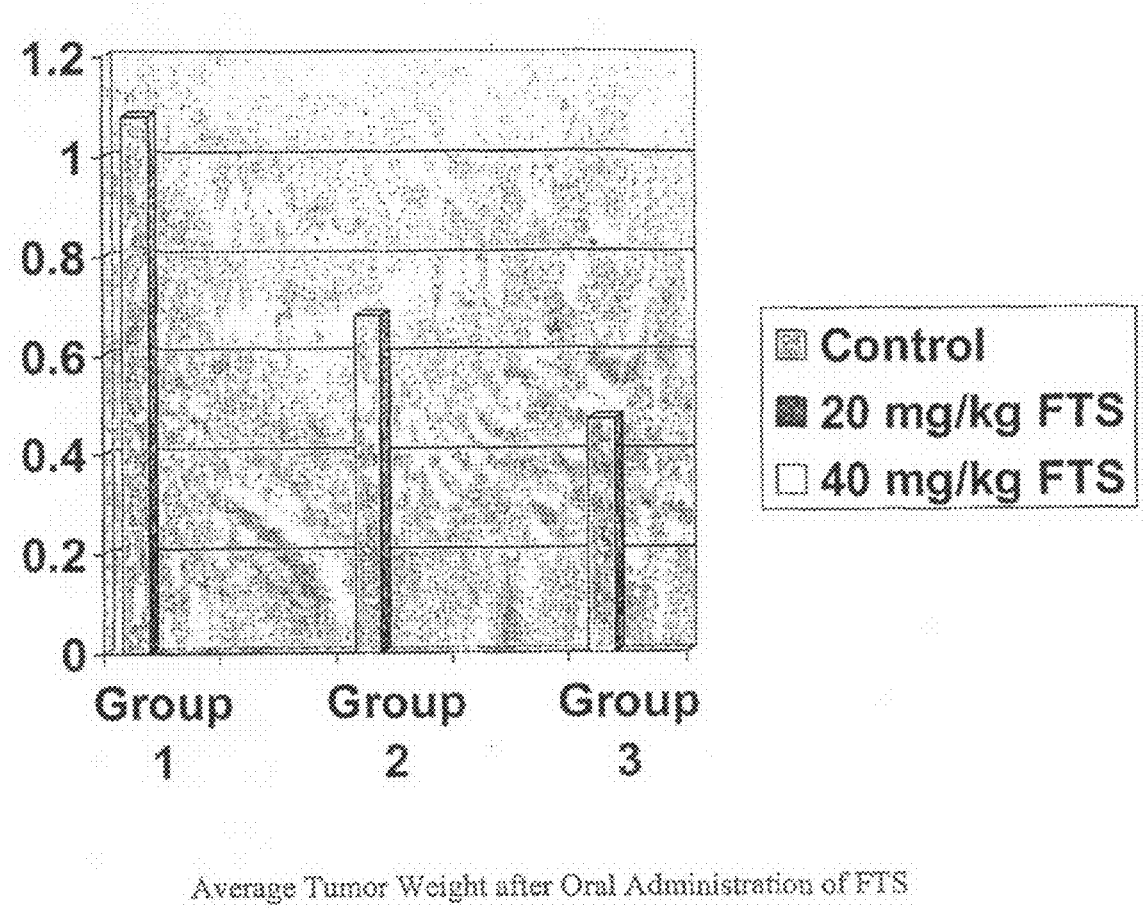
FIG. 3 is a bar graph showing average tumor weight in mice (in grams) following oral (gavage) administration of different amounts of FTS in carboxymethylcellulose, as compared to a control.

As shown in FIG. 3, average tumor weight for Group 1 (controls) was 1.02 g; average tumor weight for Group 2 (20 mg/kg FTS) was 0.68 g (32% lower than control); and average tumor weight for Group 3 (40 mg/kg FTS) was 0.47 g (53% lower than control).

EXAMPLE 3

Compatibility of FTS with Pharmaceutical Excipients

Physical mixtures (1:1 w/w) of FTS and representative pharmaceutical excipients commonly used in oral formulations were stored at 40° C./75% RH accelerated stress conditions for four weeks in loosely capped vials. Samples were assayed by HPLC at the 0, 2-week and 4-week time points. The results are shown in the table below.

TABLE

| Excipient | 0 weeks | 2 weeks | 4 weeks | Observation |
|---|---|---|---|---|
| Lactose | 97.94 | 97.23 | 98.09 | Compatible |
| Dibasic calcium phosphate | 97.95 | 95.75 | 97.08 | Compatible |
| Starch | 97.88 | 97.30 | 98.11 | Compatible |
| Hydroxypropylmethyl Cellulose | 97.93 | 98.06 | 98.12 | Compatible |
| Microcrystalline Cellulose | 97.93 | 97.72 | 98.12 | Compatible |
| Polyvinylpyrrolidone | 97.71 | 92.44 | 92.56 | Potential incompatibility |
| Croscarmellose Sodium | 97.76 | 98.14 | 98.13 | Compatible |
| Sodium Carboxymethyl Cellulose | 97.76 | 98.12 | 98.17 | Compatible |
| FTS Substance | 97.75 | 97.10 | 97.76 | |

Results of the accelerated stability evaluation demonstrated that many conventional pharmaceutical excipients may be employed in FTS tablets and capsules.

EXAMPLE 4

FTS Tablets (200 mg)

FTS active pharmaceutical ingredient (2000 g), microcrystalline cellulose (2000 g), croscarmellose sodium (200 g), and magnesium stearate (100 g) are blended to uniformity and compressed into tablets weighing 430 mg. Assuming a 5% loss on material transfers and tablet press start-up, adjustment, and shut down, approximately 9,500 FTS 200 mg tablets are yielded.

EXAMPLE 5

FTS Hard Gelatin Tablets (100 mg.)

FTS active pharmaceutical ingredient (1000 g), lactose (1000 g), microcrystalline cellulose (1000 g), and amorphous colloidal silicon dioxide (15 g) are blended to uniformity and filled into hard gelatin capsules. Assuming a 5% loss on material transfers and encapsulating machine start-up, adjustment, and shut down, approximately 9,500 FTS 100 mg capsules are yielded.

EXAMPLE 6

FTS Soft Gelatin Capsules (50 mg)

FTS active pharmaceutical ingredient (500 g), is uniformly dispersed in a mixture of corn oil (3000 g), lecithin (30 g), and Tween-80 (150 g) and filled into soft gelatin capsules. Assuming a 5% loss on material transfers and soft gelatin encapsulating machine start-up, adjustment, and shut down, approximately 9,500 FTS 50 mg soft gelatin capsules are yielded.

EXAMPLE 7

FTS Capsules (200 mg)

FTS active pharmaceutical ingredient (2841 g), microcrystalline cellulose (1421 g), starch (710 g), and magnesium stearate (29 g) are blended to uniformity and filled into size # 0 hard-shell gelatin capsules, with a fill weight of 0.357 g per capsule. Assuming a 5% loss on material transfers, encapsulation equipment startup and adjustment, approximately 13,000 FTS 200 mg capsules are yielded.

EXAMPLE 8

FTS Capsules (200 mg)

FTS active pharmaceutical ingredient (1000 g) and microcrystalline cellulose (125 g) are blended to uniformity and filled into size # 1 hard-shell gelatin capsules, with a fill weight of 0.225 g per capsule. Assuming a 5% loss on material transfers, encapsulation equipment startup and adjustment, approximately 4,750 FTS 200 mg capsules are yielded.

EXAMPLE 9

FTS Capsules (100 mg)

FTS active pharmaceutical ingredient (1000 g) and microcrystalline cellulose (125 g) are blended to uniformity and filled into size # 2 hard-shell gelatin capsules, with a fill weight of 0.112.5 g per capsule. Assuming a 5% loss on material transfers, encapsulation equipment startup and adjustment, approximately 9,500 FTS 100 mg capsules are yielded.

EXAMPLE 10

FTS Capsules (50 mg)

FTS active pharmaceutical ingredient (1000 g) and microcrystalline cellulose (125 g) are blended to uniformity and filled into size # 3 hard-shell gelatin capsules, with a fill weight of 0.056 g per capsule. Assuming a 5% loss on material transfers, encapsulation equipment startup and adjustment, approximately 18,000 FTS 50 mg capsules are yielded.

EXAMPLE 11

Bioavailability of Orally Administered FTS to Rats

Figure 4:
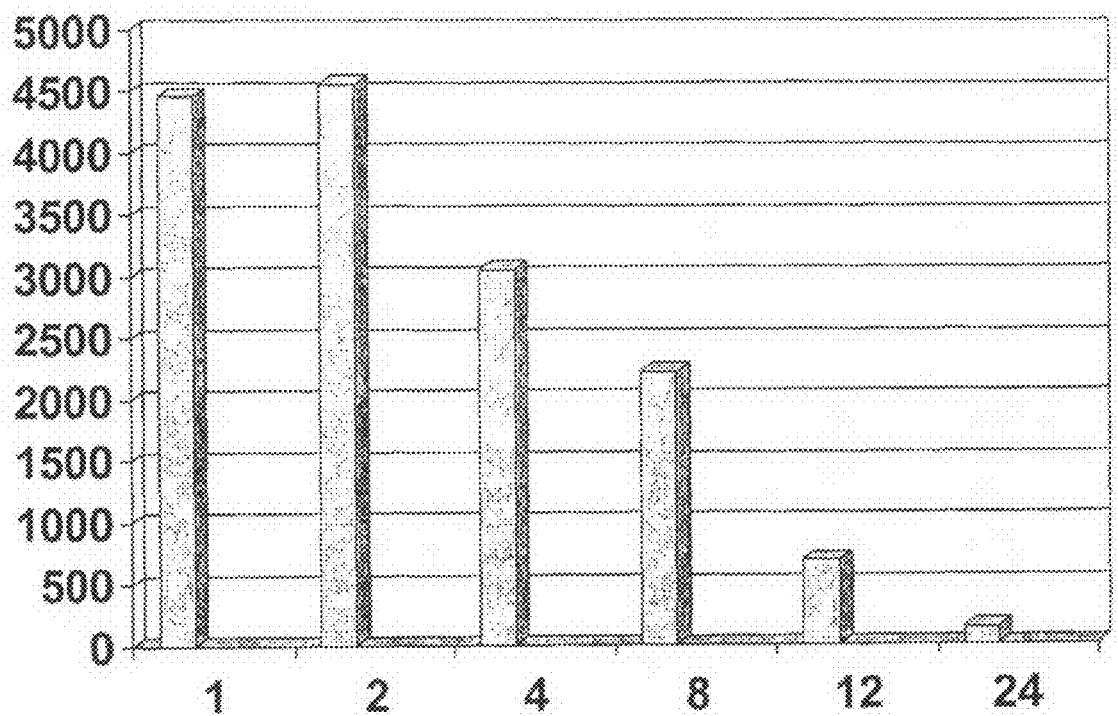
FIG. 4 is a bar graph showing FTS plasma concentration (ng/ml) over 1-24 hours after oral administration of 200 mg/kg of FTS to rats.

FTS was dissolved in a mixture of corn oil (95%) and ethanol (5%). Aliquots of the resulting solution were administered to Crl:CD(SD) (IGS)BR rats (twenty-four) at a dose of 200 mg/kg. Blood samples were collected in lithium-heparin-containing tubes via the retro-orbital plexus while under $CO_2/O_2$ anesthesia at 1, 2, 4, 8, 12 and 24 hours after dosing. Concentration of FTS at each time point was determined by LC/MS. As shown in FIG. 4, mean plasma FTS concentrations were 4454 ng/ml at 1 hour, 4550 ng/ml at 2 hours, 3047 ng/ml at 4 hours, 2216 ng/ml at 8 hours, 685 ng/ml at 12 hours, and 140 ng/ml at 24 hours. These values indicate a high level of oral bioavailability.

All patent and non-patent publications cited in this specification are indicative of the level of skill of those skilled in the art to which this invention pertains. All these publications are herein incorporated by reference to the same extent as if each individual publication or patent application were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating cancer, comprising administering to a human in need thereof an oral dosage form comprising an amount of a Ras antagonist effective to treat the cancer, and a pharmaceutically acceptable carrier other than a cyclodextrin, wherein said Ras antagonist is S-farnesyl-thiosalicylic acid as represented by the formula

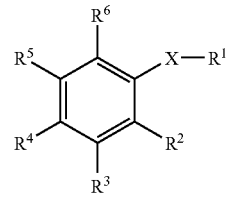

wherein:
$R^1$ represents farnesyl;
$R^2$ is $COOR^7$, wherein $R^7$ is hydrogen;
$R^3$, $R^4$, $R^5$ and $R^6$ are each independently hydrogen; and
X represents S, wherein the oral dosage form is a tablet or capsule.

2. The method of claim 1, wherein the cancer is breast cancer.

3. The method of claim 1, wherein the cancer is pancreatic cancer.

4. The method of claim 1, wherein the cancer is colon cancer.

5. The method of claim 1, wherein the cancer is lung cancer.

6. The method of claim 5, wherein the lung cancer is non-small cell lung cancer.

7. The method of claim 1, wherein the cancer is ovarian cancer.

8. The method of claim 1, wherein the cancer is prostate cancer.

9. The method of claim 1, wherein the cancer is a gioblastoma.

10. The method of claim 1, wherein the cancer is a melanoma.

* * * * *

UNITED STATES PATENT AND TRADEMARK OFFICE
CERTIFICATE OF CORRECTION

| | | |
|---|---|---|
| PATENT NO. | : 8,088,756 B2 | Page 1 of 1 |
| APPLICATION NO. | : 11/659582 | |
| DATED | : January 3, 2012 | |
| INVENTOR(S) | : Victor J. Bauer | |

It is certified that error appears in the above-identified patent and that said Letters Patent is hereby corrected as shown below:

In the Claims

Claim 9, Column 8, lines 52-53, "gioblastoma" should read -- glioblastoma --.

Signed and Sealed this
Fourteenth Day of January, 2014

Michelle K. Lee
*Deputy Director of the United States Patent and Trademark Office*